US012642604B2

(12) United States Patent (10) Patent No.: US 12,642,604 B2
Mannion et al. (45) Date of Patent: Jun. 2, 2026

(54) PHYSICIAN ENABLED LASER CONTROL FROM URETEROSCOPE HANDLE

(71) Applicant: C. R. Bard, Inc., Franklin Lakes, NJ (US)

(72) Inventors: Paul Thomas Mannion, Eliot, ME (US); Tony Garvey, Listowel (IE); Padraig Fogarty, Ballina-Killaloe (IE)

(73) Assignee: C. R. Bard, Inc., Franklin Lakes, NJ (US)

( * ) Notice: Subject to any disclaimer, the term of this patent is extended or adjusted under 35 U.S.C. 154(b) by 153 days.

(21) Appl. No.: 18/563,864

(22) PCT Filed: May 11, 2022

(86) PCT No.: PCT/US2022/028697
§ 371 (c)(1),
(2) Date: Nov. 22, 2023

(87) PCT Pub. No.: WO2022/250958
PCT Pub. Date: Dec. 1, 2022

(65) Prior Publication Data
US 2024/0225756 A1 Jul. 11, 2024

Related U.S. Application Data

(60) Provisional application No. 63/192,717, filed on May 25, 2021.

(51) Int. Cl.
*A61B 34/00* (2016.01)
*A61B 1/00* (2006.01)
(Continued)

(52) U.S. Cl.
CPC .......... *A61B 34/25* (2016.02); *A61B 1/00066* (2013.01); *A61B 1/307* (2013.01);
(Continued)

(58) Field of Classification Search
CPC ..... A61B 34/25; A61B 34/74; A61B 1/00066; A61B 2017/00199; A61B 18/26
See application file for complete search history.

(56) References Cited

U.S. PATENT DOCUMENTS

2006/0058617 A1* 3/2006 Sano .................... A61B 1/3132
600/407
2007/0219806 A1 9/2007 Yamaki
(Continued)

FOREIGN PATENT DOCUMENTS

WO 2022208462 A1 10/2022
WO 2022250958 A1 12/2022

OTHER PUBLICATIONS

PCT/US2022/028697 filed May 11, 2022 International Search Report and Written Opinion dated Oct. 20, 2022.
(Continued)

*Primary Examiner* — Aaron B Fairchild
(74) *Attorney, Agent, or Firm* — Rutan & Tucker LLP

(57) ABSTRACT

A system for providing a medical treatment, including a first medical instrument and a second medical instrument is disclosed. The first medical instrument includes a first operator interface configured to define a plurality of operating parameters of the first medical instrument. The second medical instrument includes a second operator interface configured to define a subset of the plurality of operating parameters. The first operator interface is configured for placement and use outside of a sterile field and the second operator interface is configured for placement and use within the sterile field. The second operator interface is attached to or attachable to a handle of the second medical instrument. The handle is configured for manipulation by a hand of the operator and the second operator interface is configured for interaction with one or more extremities of the same hand.

17 Claims, 6 Drawing Sheets

(51) Int. Cl.

| | |
|---|---|
| *A61B 1/307* | (2006.01) |
| *A61B 18/26* | (2006.01) |
| *A61B 17/00* | (2006.01) |
| *A61B 18/00* | (2006.01) |

(52) U.S. Cl.
CPC .............. *A61B 18/26* (2013.01); *A61B 34/74* (2016.02); *A61B 2017/00199* (2013.01); *A61B 2017/00221* (2013.01); *A61B 2017/00973* (2013.01); *A61B 2018/00511* (2013.01); *A61B 2018/00916* (2013.01); *A61B 2018/00982* (2013.01)

(56) References Cited

U.S. PATENT DOCUMENTS

| | | | |
|---|---|---|---|
| 2014/0243849 A1 | 8/2014 | Saglam et al. |
| 2019/0008601 A1 | 1/2019 | Pereira et al. |
| 2019/0110845 A1 | 4/2019 | Yang |
| 2020/0353280 A1 | 11/2020 | Yang et al. |
| 2021/0038306 A1 | 2/2021 | McLoughlin et al. |

OTHER PUBLICATIONS

EP 25207884.5 filed Oct. 10, 2025 Extended European Search Report dated Feb. 16, 2026.

* cited by examiner

PHYSICIAN ENABLED LASER CONTROL FROM URETEROSCOPE HANDLE

PRIORITY

This application is a U.S. national stage application of International Application No. PCT/US2022/028697, filed May 11, 2022, which claims the benefit of priority to U.S. Provisional Application No. 63/192,717, filed May 25, 2021, each of which is incorporated by reference in its entirety into this application.

BACKGROUND

Proper aseptic technique is one of the most fundamental and essential principles of infection control in the clinical and surgical setting. Creating and maintaining a sterile field is an essential component of aseptic technique. A sterile field is an area created by placing sterile surgical drapes around the patient's surgical site and on a stand that will hold sterile instruments and other items needed during treatment. A healthcare worker dons proper sterile surgical attire to enter the sterile field. Only sterile objects and personnel may be allowed within the sterile field. When a sterile field is created around a procedure site, items below the level of the draped client, such as items on the floor, are outside the sterile field and are not sterile. Only sterile items are free of potential infectious agents, and once a sterile object comes in contact with a non-sterile object, such as equipment, surfaces, or a person, outside of the sterile field, that object is no longer sterile. For example, if a healthcare worker touches a piece of equipment outside the sterile field with a gloved hand, that hand is no longer sterile and thus is no longer aloud within the sterile field.

Laser energy is used in a wide variety of medical procedures, including urology, neurology, otorhinolaryngology, ophthalmology, gastroenterology, cardiology, and gynecology. Various procedures, and even different portions of the same procedure, often require different levels and intensities of laser energy, which are delivered to cauterize, ablate, break-up, or otherwise treat tissue or other material in a patient. Generally, a user may control and/or modify the settings for the laser energy by inputting or adjusting the settings on a hand-based control module through buttons, dials, or a graphical user interface having a touch screen. However, in a surgical setting, the user usually is holding at least one medical device in his or her hands and may not be within arm's reach of the control module, which may increase the time and/or the number of medical professionals required during the procedure. Moreover, touching components outside of the sterile field (e.g., the control module) while also performing the procedure introduces sterilization and cleanliness issues. The chances of user error are also increased, further complicating and prolonging the procedure and exposing the patient to greater risk.

Systems, devices, and methods disclosed herein may help overcome some of the complications and patient risks described above by providing an operator with a greater level of control of a laser instrument from within the sterile field.

SUMMARY

Briefly summarized, disclosed herein is a system for providing a medical treatment, including a first medical instrument and a second medical instrument. The first medical instrument includes a first control module, and a first patient interface member coupled with the control module. The patient interface member includes a first distal end configured to engage a patient body. The first medical instrument further includes a first operator interface operatively coupled to the control module, wherein the first operator interface is configured to define a plurality of operating parameters of the first medical instrument. The first operator interface is also configured to selectively activate and deactivate the first medical instrument in accordance with providing the medical treatment.

The second medical instrument includes a second control module and a second patient interface member coupled with the second control module. The second patient interface member includes a second distal end configured to engage the patient body and a handle coupled with the second patient interface member. The handle is configured to be grasped by a hand of the operator, and manipulation of the handle causes operations of the second distal end. The handle includes a second operator interface, and the second operator interface is configured to define a subset of the plurality of operating parameters of the first medical instrument. In use, the first patient interface member may be coupled with the second patient interface member and the first distal end may be disposed adjacent the second distal end.

The second medical instrument may be an endoscope or more specifically a ureteroscope, and the first medical instrument may include a laser such as a laser optical fiber disposed within the second patient interface member. The first operator interface may include a graphical user interface configured for defining the plurality of operating parameters. The first operator interface may also include a foot pedal interface configured for the selective activation and deactivation of the first medical instrument. In use, the first operator interface is disposed outside of a sterile field, and the handle is disposed within the sterile field.

In some embodiments, operations caused by the manipulation of the handle include steering the second distal end toward a treatment location of the patient body, and steering the second distal end includes movement of an actuator attached to the handle. Movement of the actuator may be performed with one or more extremities of the operator's hand, and defining one or more of the plurality of operating parameters of the first medical instrument via the second operator interface may be performed with one or more extremities of the same hand.

The plurality of operating parameters may include one or more of:

changing a state of the first medical instrument between a standby state and an active state;

selectively enabling and disabling the second operator interface;

adjusting a laser pulse energy;

adjusting a laser pulse frequency;

adjusting a laser pulse width;

adjusting an average power of the laser;

changing a state of a laser aiming beam of the first medical instrument between on, off, and blinking states; or adjusting an intensity of the aiming beam.

The subset of the plurality of operating parameters includes one or more of:

changing the state of the first medical instrument between a standby state and an active state;

selectively enabling and disabling the second operator interface;

adjusting the laser pulse energy;

adjusting the laser pulse frequency;

adjusting the laser pulse width;

adjusting the average laser power;

changing the state of the laser aiming beam between the on, off, and blinking states; or adjusting the aiming beam intensity.

In some embodiments, the second operator interface is coupled with the first control module via a wireless connection and the second operator interface may include a scrolling device and a selecting device. In some embodiments, the second operator interface is selectively attachable to the handle.

Also disclosed herein is an endoscope, including a control module and an elongate shaft coupled with the control module. The shaft is configured for insertion within a patient body, and the shaft includes a working channel extending along a length of the shaft. A handle at a proximal end of the shaft includes an operator interface configured to: (i) communicatively couple with a separate medical instrument; and (ii) define a set of operating parameters of the separate medical instrument.

In some embodiments, the endoscope is a ureteroscope and in use, a fiber optic laser of the instrument may be inserted through the working channel. In use, the handle may be disposed within the sterile field. The shaft may include a steering mechanism configured to articulate a distal portion of the shaft, and the handle may include an actuator operatively coupled with the steering mechanism. In use, movement of the actuator is performed with one or more extremities of the operator's hand while grasping the handle, and defining the set of operating parameters via the operator interface is performed with one or more extremities of the same hand. The set of operating parameters may include one or more of:

changing a state of the instrument between a standby state and an active state;

selectively enabling and disabling the operator interface;

adjusting a pulse energy of a laser;

adjusting a pulse frequency of the laser;

adjusting a pulse width of the laser;

adjusting an average power of the laser;

changing a state of a laser aiming beam of the instrument between on, off, and blinking states; or adjusting an intensity of the aiming beam.

The operator interface may be wirelessly coupled with a control module of the instrument and the operator interface may include a scrolling device and a selecting device. In some embodiments, the operator interface is selectively attachable to the handle.

Also disclosed herein is a medical instrument for performing a lithotripsy procedure, including a control module and an elongate shaft coupled with the control module. A laser of the instrument includes a laser optical fiber extending along a length of the shaft, and an operator interface is operatively coupled with the control module. The operator interface includes: (i) a graphical user interface for defining a plurality of operating parameters of the instrument; (ii) a foot pedal interface for selectively activating and deactivating the instrument in accordance with performing the lithotripsy procedure; and (iii) a remote interface configured to define a subset of the plurality of operating parameters.

The shaft may be configured for insertion within a working channel of a ureteroscope. In use, the graphical user interface is disposed outside of a sterile field, while the remote interface is disposed within the sterile field.

The remote interface may be wirelessly coupled with the control module and may include a scrolling device and a selecting device. In some embodiments, the remote interface is selectively attachable to a handle of the ureteroscope.

The plurality of operating parameters includes one or more of:

changing a state of the instrument between a standby state and an active state;

selectively enabling and disabling the remote interface;

adjusting a pulse energy of the laser;

adjusting a pulse frequency of the laser;

adjusting a pulse width of the laser;

adjusting an average power of the laser;

changing a state of a laser aiming beam of the instrument between on, off, and blinking states; or adjusting an intensity of the aiming beam.

The subset of operating parameters includes one or more of:

changing a state of the instrument between a standby state and an active state;

selectively enabling and disabling the remote interface;

adjusting the pulse energy of the laser;

adjusting the pulse frequency of the laser;

adjusting the pulse width of the laser;

adjusting the average power of the laser;

changing the state of the laser aiming beam between the on, off, and blinking states; or adjusting the aiming beam intensity.

In use, interaction with the remote interface is performed with one or more extremities of the operator's hand while grasping the handle of the ureteroscope with the same hand.

Also disclosed herein is a method of performing a medical treatment within a urinary tract of a patient. The method includes advancing an elongate shaft of a ureteroscope along the urinary tract of the patient to a treatment location and inserting a laser shaft of a laser medical instrument through a working channel of the ureteroscope. The method further includes defining a plurality of operating parameters of the instrument via a graphical user interface of the instrument, activating the instrument via a foot pedal interface of the instrument, and adjusting a subset of the plurality of operating parameters via a remote interface of the instrument.

In some embodiments of the method, the remote interface is attached to a handle of the ureteroscope. The method may further include locating the graphical user interface outside of a sterile field and locating the remote interface within the sterile field. The method may further include grasping the handle of the ureteroscope with one hand of an operator and engaging the remote interface with one or more extremities of the same hand while grasping the handle. In some embodiments, the method further includes manipulating a steering actuator of the ureteroscope to articulate a distal portion of the elongate shaft with one or more extremities of the same hand.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The directional terms "proximal" and "distal" are used herein to refer to opposite locations on a medical device. The proximal end of the device is defined as the end of the device closest to the end-user when the device is in use by the end-user. The distal end is the end opposite the proximal end, along the longitudinal direction of the device, or the end furthest from the end-user.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Figure 1:
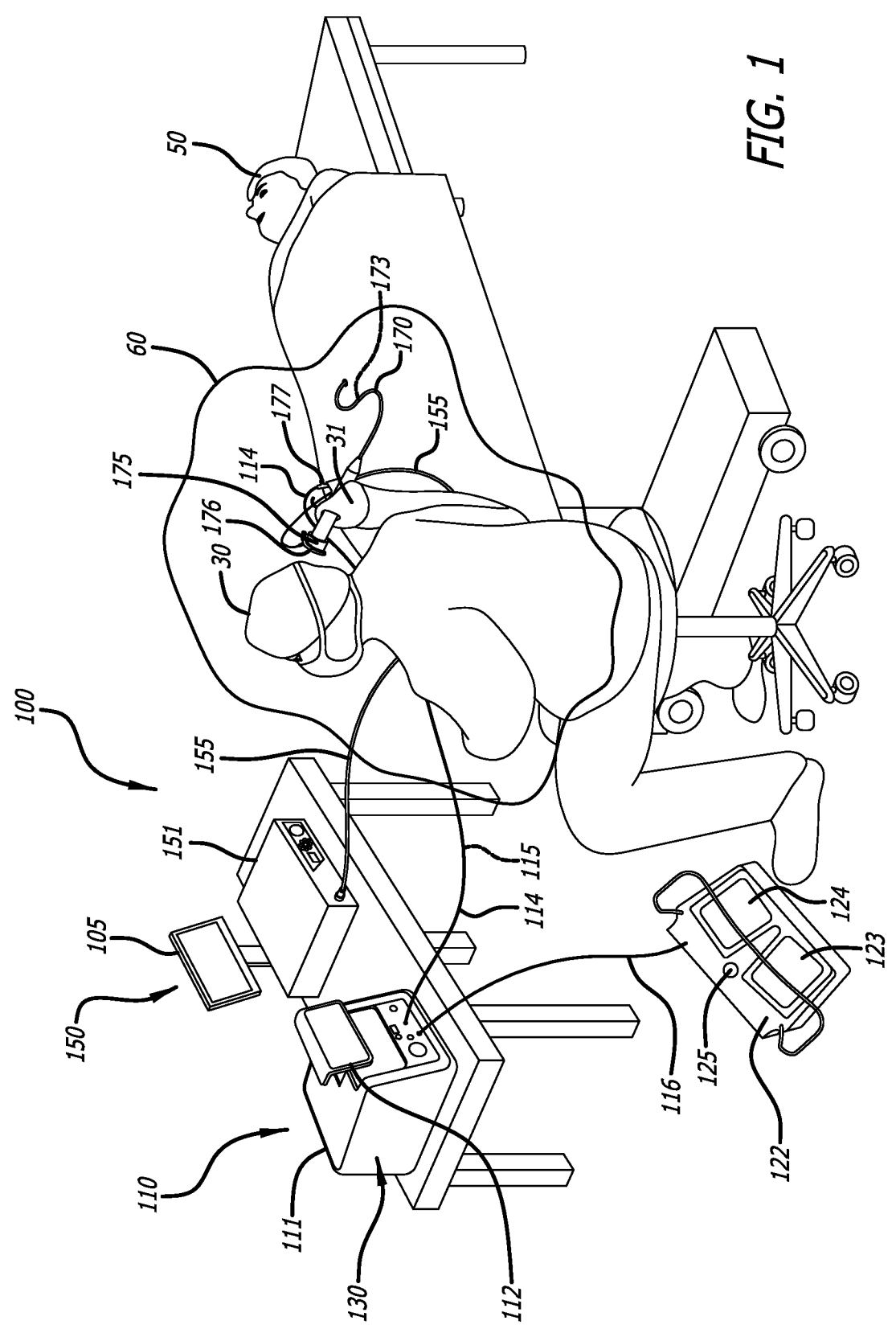
FIG. 1 illustrates a current embodiment of a medical system within a medical treatment environment.

FIG. 1 illustrates a current embodiment of a medical system 100 shown within a medical treatment environment. An operator 30 (e.g., a doctor) is shown performing an invasive treatment on a patient 50 within a sterile field 60. The system 100 includes two separate medical instruments, i.e., a first medical instrument 110 and a second medical instrument 150. The treatment is such that simultaneous operation of the two medical instruments enhances the outcome of the treatment. In the illustrated current embodiment, the first medical instrument 110 is a urological surgery laser instrument (hereinafter referred to as the laser instrument 110) and the second medical instrument 150 is a ureteroscope (hereinafter referred to as the ureteroscope 150).

The laser instrument 110 includes a laser control module 111 operatively coupled with a flexible laser shaft 114. The laser shaft 114 includes a fiber optic laser 115 configured to define a laser beam projected away from a distal end of the laser shaft 114. During operation the laser 115 is fired (i.e., activated) to turn "on" the laser beam.

The laser instrument 110 includes a graphical user interface (GUI) 112 via which the operator 30 or an assistant may define a plurality of operating parameters of the laser instrument 110. The laser instrument 110 also includes a foot pedal interface 122 interface including a left foot pedal 123, a right foot pedal 124 and a state button 125. The foot pedal interface 122 is coupled with the control module 111 via a foot pedal connection wire 116. As illustrated in FIG. 1, the laser control module 111 and the foot pedal interface 122 are disposed outside of the sterile field 60. The laser shaft 114 extends across a barrier of the sterile field 60.

The control module 111 includes logic 130 as described in relation to a state diagram shown in Table 1 below. The laser instrument 110 may generally be disposed in an active state and a standby state. Pressing the state button 125 toggles the laser instrument 110 between the active state and the standby state. The left and right foot pedals 123, 124 are disabled when the laser instrument 110 is disposed in the standby state. When the laser instrument 110 is disposed in the active state, pressing the left foot pedal fires the laser 115 in accordance with a left-pedal set of parameter settings, and pressing the right foot pedal fires the laser 115 in accordance with a right-pedal set of parameter settings.

TABLE 1

| Operating States of the Laser Instrument 110 | | | |
| --- | --- | --- | --- |
| STATE | STATE BUTTON | LEFT PEDAL | RIGHT PEDAL |
| Standby | Switches system to the active state | Disabled | Disabled |
| Active | Switches system to the standby state | Fires laser at left pedal settings | Fires laser at right pedal settings |

With further reference to the FIG. 1, the ureteroscope 150 includes ureteroscope control module 151 operatively coupled with an elongate flexible shaft 170 configured for insertion within a urinary tract of the patient 50. The shaft 170 includes a camera (not shown) at a distal end of the shaft 170. During operation, images acquired by the camera are rendered on a display 105 coupled with the ureteroscope control module 151. A working channel 173 extends along the shaft 170, and an access port 177 provides access to the working channel 173 at a proximal end of the shaft 170.

A handle 175 is coupled to the shaft 170 at the proximal end of the shaft 170. The handle 175 is configured for manipulation of the shaft 170 during use. The handle 175 includes a steering actuator 176 operatively coupled with an articulating distal portion (not shown) of the shaft 170 so that manipulation of the actuator 176 articulates the distal portion of the shaft 170. A wire 155 couples the handle 175 with the ureteroscope control module 151. As shown in FIG. 1, the ureteroscope control module 151 and the display 105 are disposed outside of the sterile field 60. The handle 175 and shaft 170 are disposed within the sterile field and as such, the wire 155 extends across the barrier of the sterile field 60. As shown in FIG. 1, an upper portion of the operator 30 including the hands 31 are disposed within the sterile field 60, and a lower portion of the operator 30 include the feet are disposed outside the sterile field 60.

During the treatment, the flexible shaft 170 of the ureteroscope 150 is inserted into the urinary tract of the patient 50 to a treatment location. The flexible laser shaft 114 is inserted into the working channel 173 of the shaft 170 via the access port 177. The ureteroscope control module 151 renders images on the display 105 as acquired via the camera at the distal end of the shaft 170. The images show tissue and other objects (e.g., a kidney stone) at the treatment location. The operator 30 performs the treatment via operation of the laser instrument 110 while viewing the images acquired and displayed by the ureteroscope 150.

A treatment procedure may typically include positioning the working distal end of the laser shaft 114 at a desired location as verified by the acquired images. Manipulation of the laser shaft 114 is typically preformed via manipulation of the shaft 170 of the ureteroscope 150. More specifically, the operator 30 grasps and manipulates the handle 175 to position the distal end of the shaft 170 thereby positioning the distal end the laser shaft 114 which is disposed within the working channel 173. The operator 30 may adjust the insertion depth of the shaft 170 and may also adjust a rotational position of the shaft 170. The operator 30 may also manipulate the steering actuator 176 to articulate the distal portion of the shaft 170. Articulation of the distal portion of the shaft 170 may effectively point the distal end of the laser instrument 110 toward a desired object for ablation or surgery.

After establishing the desired position and orientation of the distal end of the laser instrument 110, the operator 30 may press the left foot pedal 123 or right foot pedal 124 to fire the laser 115 in accordance with the treatment. In some instances, it may be desirable to adjust one or more operating parameters of the laser instrument 110 after initiation of the treatment. In such instances, touching the GUI 112 may be necessary by the operator 30 or an assistant. Standard aseptic technique requires the upper portion of the operator (i.e., the portion within the sterile field 60) to remain within the sterile field 60 through the duration of the treatment. As such, typical practice includes instructing an assistant to make the parameter adjustments after which the operator 30 may verify the parameter adjustments by viewing the GUI 112.

Figure 2A:
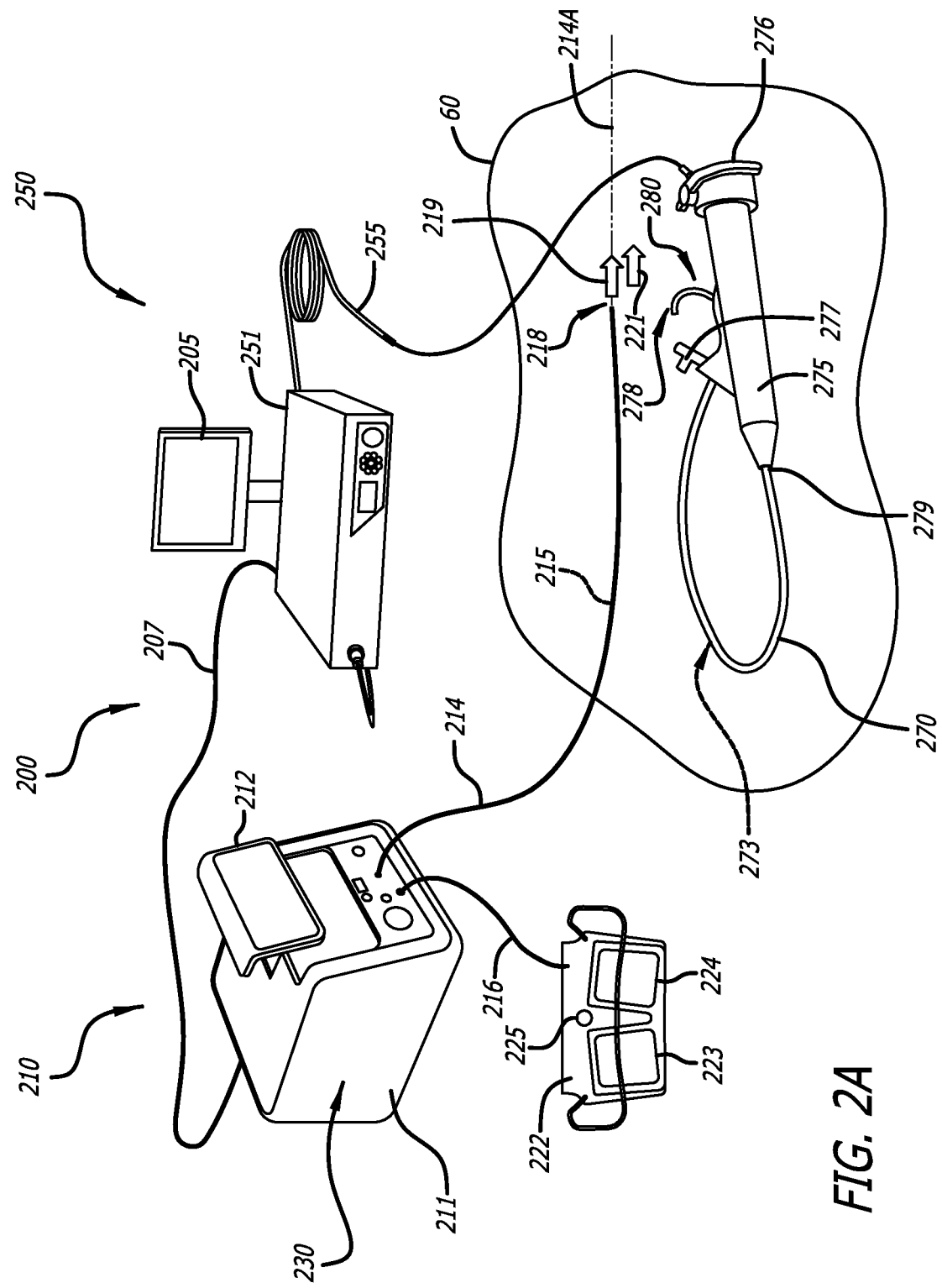
FIG. 2A illustrates a first embodiment of an improved medical system, in accordance with some embodiments.

FIG. 2A illustrates a first embodiment of an improved medical system, in accordance with some embodiments. The medical system 200 includes two medical instruments, i.e., a first medical instrument 210 and a second medical instrument 250 communicatively coupled together. By way of example in the illustrated embodiment, the first medical instrument 210 may be a urological surgery laser instrument (hereinafter referred to as the laser instrument 210) and the second medical instrument 250 may an endoscope or more specifically a ureteroscope (hereinafter referred to as the ureteroscope 250). However, the first medical instrument 210 and a second medical instrument 250 may be any two medical instruments used in combination with each other to perform a medical procedure.

The laser instrument 210 includes a laser control module 211 operatively coupled with a flexible laser shaft 214. The laser shaft 214 includes a fiber optic laser 215 configured to define a laser beam 219 at the distal end 218 of the laser shaft

214. During operation the laser 215 is fired (i.e., activated to start operation laser beam 219 and deactivated to stop operation of the laser beam 219). The laser beam 219 may be directed distally away from a distal end 218 as shown. In other words, the laser beam 219 may be coincident with a distal extension of a longitudinal axis 214A of the laser shaft 214 at the distal end 218. The laser instrument 210 may also include an aiming light beam 221 directed distally away from a distal end 218 as shown. The aiming beam 221 provides a visual indication of the aiming point of the laser beam 219. In other words, the aiming beam 221 may generate a visible indication (e.g., a dot on the tissue or foreign substance) of an impact location of the laser beam 219. In use, the operator may observe the dot via images provide by the ureteroscope 250.

The laser instrument 210 may include a graphical user interface (GUI) 212 via which the operator, such as the operator 30 depicted in FIG. 1, or an assistant may define a plurality of operating parameters for the laser instrument 210. The laser instrument 210 may also include a foot pedal interface 222 including a left foot pedal 223, a right foot pedal 224 and a state button 225. The foot pedal interface 222 may be coupled with the laser control module 211 via a foot pedal connection wire 216. In some embodiments, the foot pedal interface 222 may be wirelessly coupled with the laser control module 211. As illustrated in FIG. 2A, the laser control module 211 and the foot pedal interface 222 are configured for operation outside of the sterile field 60. The laser shaft 214 may be sterilized and as such is configured for placement and use within the sterile field 60. In use, laser shaft 214 extends across the barrier of the sterile field 60.

With further reference to the FIG. 2A, the ureteroscope 250 includes a ureteroscope control module 251 operatively coupled with an elongate flexible shaft 270 configured for insertion within a urinary tract of the patient 50 (FIG. 1). The shaft 270 includes a camera (not shown) at a distal end 278 of the shaft 270. During operation, images acquired by the camera are rendered on a display 205 coupled with the ureteroscope control module 251. A working channel 273 extends along the shaft 270, and an access port 277 provides access to the working channel 273 at a proximal end 279 of the shaft 270.

A handle 275 is coupled to the shaft 270 at the proximal end 279 of the shaft 270. The handle 275 is configured for manipulation of the shaft 270 during use. The handle 275 includes a steering actuator 276 operatively coupled with an articulating distal portion (not shown) of the shaft 270, so that manipulation of the actuator 276 articulates the distal portion 278 of the shaft 270. A connection wire 255 couples the handle 275 with the ureteroscope control module 251. The ureteroscope control module 251 and the display 205 are configured for placement and use outside of the sterile field 60. The handle 275 and the shaft 270 are sterilized and are thus configured for placement and use within the sterile field 60. In use, the wire 255 extends across the barrier of the sterile field 60.

The laser instrument 210 and the ureteroscope 250 are communicatively coupled with each other. In the illustrated embodiment, the laser instrument 210 and the ureteroscope 250 are coupled together via a coupling wire 207. In other embodiments, the laser instrument 210 and the ureteroscope 250 may be wirelessly coupled together.

Figure 2B:
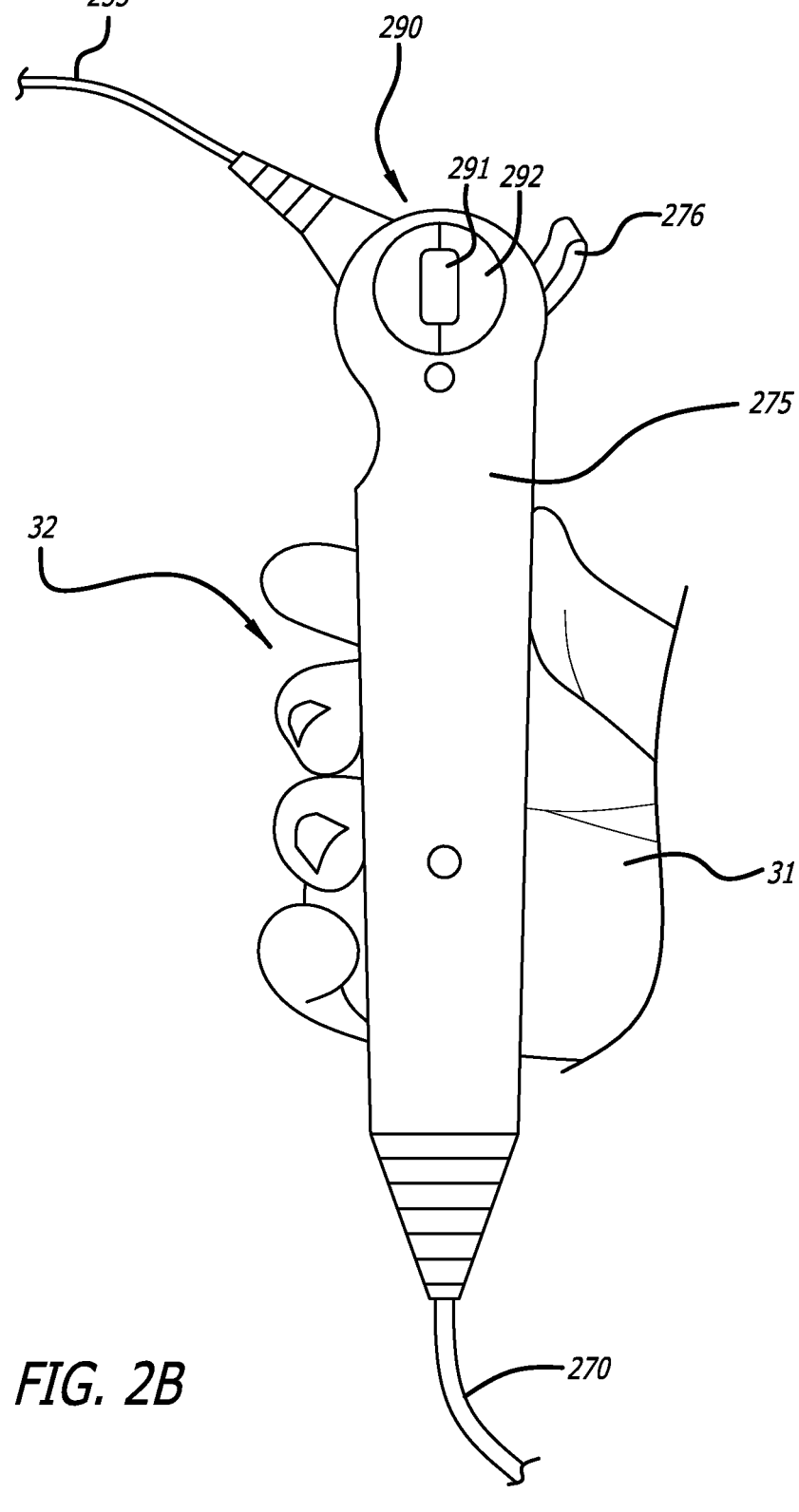
FIG. 2B is a detailed illustration of a handle of a second medical instrument of the system of FIG. 2A, in accordance with some embodiments.

FIG. 2B is a detailed illustration of the handle 275, in accordance with some embodiments. The handle 275 is configured to be grasped by the hand 31 of the operator. The steering actuator 276 is configured for manipulation by one or more extremities 32 of the hand 31, such as the thumb, for example. The handle 275 includes a remote interface 290 including a scrolling device 291 (e.g., a thumb wheel) and a selecting device 292 (e.g., a button). The scrolling device 291 and a selecting device 292 are configured for manipulation by one or more extremities 32 of the hand 31, such as the thumb, for example. The remote interface 290 is coupled with the laser instrument 210 or more specifically, the laser control module 211.

Operation of the scrolling device 291 may include scrolling through screens, scrolling through parameters, incrementing/decrementing parameter values, and the like. Operation of the selecting device 291 may include toggling the laser instrument 210 between states, selecting parameters, and/or selecting parameter values. The remote interthe state button 225 toggles the laser system 210 between the active state and the standby state. The left and right foot pedals 223, 224 are disabled when the laser instrument 210 is disposed in the standby state. When the laser instrument 210 is disposed in the active state, pressing the left foot pedal fires the laser 215 in accordance with a left-pedal set of parameter settings, and pressing the right foot pedal fires the laser 215 in accordance with a right-pedal set of parameter settings. In some embodiments, the logic 230 may allow for the remote interface 290 (i.e., the selecting device 292) to toggle the laser instrument 210 between the active sate and the standby state. In some embodiments, the logic 230 may also allow for the remote interface 290 to toggle the laser instrument 210 between the disabled remote interface state and the enabled remote interface state.

TABLE 2

| Operating States of the Laser Instrument 210 | | | | | |
| --- | --- | --- | --- | --- | --- |
| Remote Interface | Instrument | Foot pedal interface | | | |
| State | State | State Button | Left Pedal | Right Pedal | Remote Interface |
| Disabled | Standby | Switches instrument to the active state | Disabled | Disabled | Disabled (parameter adjustment via GUI allowed) |
| | Active | Switches instrument to the standby state | Fires laser at left pedal settings | Fires laser at right pedal settings | Disabled (no parameter adjustment allowed) |
| Enabled | Standby | Switches instrument to the active state | Disabled | Disabled | Enabled (parameter adjustment via remote interface allowed) |
| | Active | Switches instrument to the standby state | Fires laser at left pedal settings | Fires laser at right pedal settings | Disabled (no parameter adjustment allowed) | face 290 is coupled with the laser control module 211. In the illustrated embodiment, the remote interface 290 is connected to the laser control module 211 via a wired connection extending along the connection wire 255, through the ureteroscope control module 251, and along the coupling wire 207 to the laser control module 211. In some embodiments, the remote interface 280 may be wirelessly coupled with the laser control module 211.

The Table 2 below illustrates a logic state diagram of the laser instrument 210, in accordance with some embodiments. The control module 211 includes logic 230 (FIG. 2A) as described below in relation to the state diagram shown in Table 2. The logic 230 may provide for selective enabling and disabling of the remote interface 290 via the GUI 212. When the remote interface 290 is disabled by the logic 230, manipulation of the scrolling device 291 or the selecting device 292 has no operational effect on the laser instrument 210. In other words, when the remote interface 290 is disabled, operating parameter adjustment of the laser instrument 210 is allowed via the GUI 212 and prevented via the remote interface 280. When the remote interface 290 is enabled by the logic 230, adjustment of the operating parameters via the GUI 212 is prevented, and adjustment of a subset of the operating parameters via the remote interface 280 is allowed.

The logic 230 may provide for disposition of the laser instrument 210 between the standby state and the active state via the foot pedal interface 222 as shown in Table 2. Pressing The logic 230 may also define a plurality of operating parameters that may be defined/adjusted via the GUI 212. The plurality of operating parameters may include:

changing the state of the laser instrument between the standby state and an active state;

selectively enabling and disabling the remote interface;

adjusting a pulse energy of the laser 215;

adjusting a pulse frequency of the laser 215;

adjusting a pulse width of the laser 215;

adjusting an average power of the laser 215;

changing a state of the laser aiming beam 221 between on, off, and blinking states; and adjusting an intensity of the aiming beam 221.

The logic 230 may also define a subset of the plurality of operating parameters that may be adjusted via the remote interface 290. The subset of the plurality of operating parameters may include:

changing a state of the laser instrument between the standby state and the active state;

selectively enabling and disabling the remote interface;

adjusting a pulse energy of the laser 215;

adjusting a pulse frequency of the laser 215;

adjusting a pulse width of the laser 215;

adjusting an average power of the laser 215;

changing a state of a laser aiming beam 221 between on, off, and blinking states; and adjusting an intensity of the aiming beam 221.

During the treatment, the flexible shaft 270 of the ureteroscope 250 is inserted into the urinary tract of the patient 50 to a treatment location. The flexible laser shaft 214 is inserted into the working channel 273 of the shaft 270 via the access port 277. In some instances, flexible laser shaft 214 may be inserted so that the distal end 218 of the laser shaft 214 is disposed adjacent the distal end 278 of the shaft 270. The ureteroscope control module 251 renders images on the display 205 as acquired via the camera at the distal end of the shaft 270. The images show tissue and other objects (e.g., a kidney stone) at the treatment location. The operator performs the treatment via operation of the laser instrument 210 while viewing the images acquired and displayed by the ureteroscope 250.

A method of using the system 200 in accordance with a treatment procedure may include positioning the working distal end of the laser shaft 214 at a desired location within the urinary tract. The operator may verify the position of the distal end 218 of the laser shaft 214 by viewing images acquired and displayed by the ureteroscope 250. The operator may grasp and manipulate the handle 275 to adjust the position the distal end 278 of the shaft 270 and, by association, the distal end 218 of the laser shaft 214. The operator may adjust the insertion depth of the shaft 270 and may also adjust a rotational position of the shaft 270 within the urinary tract. The operator 30 may also manipulate the steering actuator 276 to articulate the distal portion 280 of the shaft 270. Articulation of the distal portion 280 of the shaft 270 may effectively point the laser beam 219 toward a desired object for ablation or surgery. The operator may also adjust the inserted position of the laser shaft 214 within the working channel 273 so that the distal end 218 of the laser shaft 214 extends a desired distance beyond the distal end 278 of the shaft 270.

After establishing the desired position and orientation of the distal end 218 of the laser instrument 210, the operator may press the left foot pedal 223 or right foot pedal 224 to fire the laser 215 in accordance with the treatment. The operator may then adjust the position and/or orientation of the distal end 218 and fire the laser 215 again. During the course of the treatment, the operator may repeatedly adjust the position and/or orientation the distal end 218 and fire the laser 215.

The method may also include defining a plurality of operating parameters of the laser instrument 210 prior to initiation of the treatment. The operating parameters may be defined via the GUI 212. After defining the operating parameters via the GUI 212, the operator or an assistant may enable the remote interface 290 via the GUI 212 or the remote interface 290. In some instances, it may be desirable to adjust one or more operating parameters of a subset of the plurality of operating parameters of the laser instrument 210 after initiation of the treatment. In such instances, the operator may utilize the remote interface 290 to make the adjustments from within the sterile field 60. The operator may toggle the instrument 210 to the standby state by pressing the mode button 225 with a foot outside of the sterile field 60 or the selecting device 292 of the remote interface 290. With the remote interface 290 enabled, the operator may personally (i.e., without assistance from any other person) adjust one or more operating parameters of the subset via the scrolling device 291 and the selecting device 292 without breaching the sterile field 60. Thereafter, the operator may toggle the laser instrument 210 to the active state.

Figure 3A:
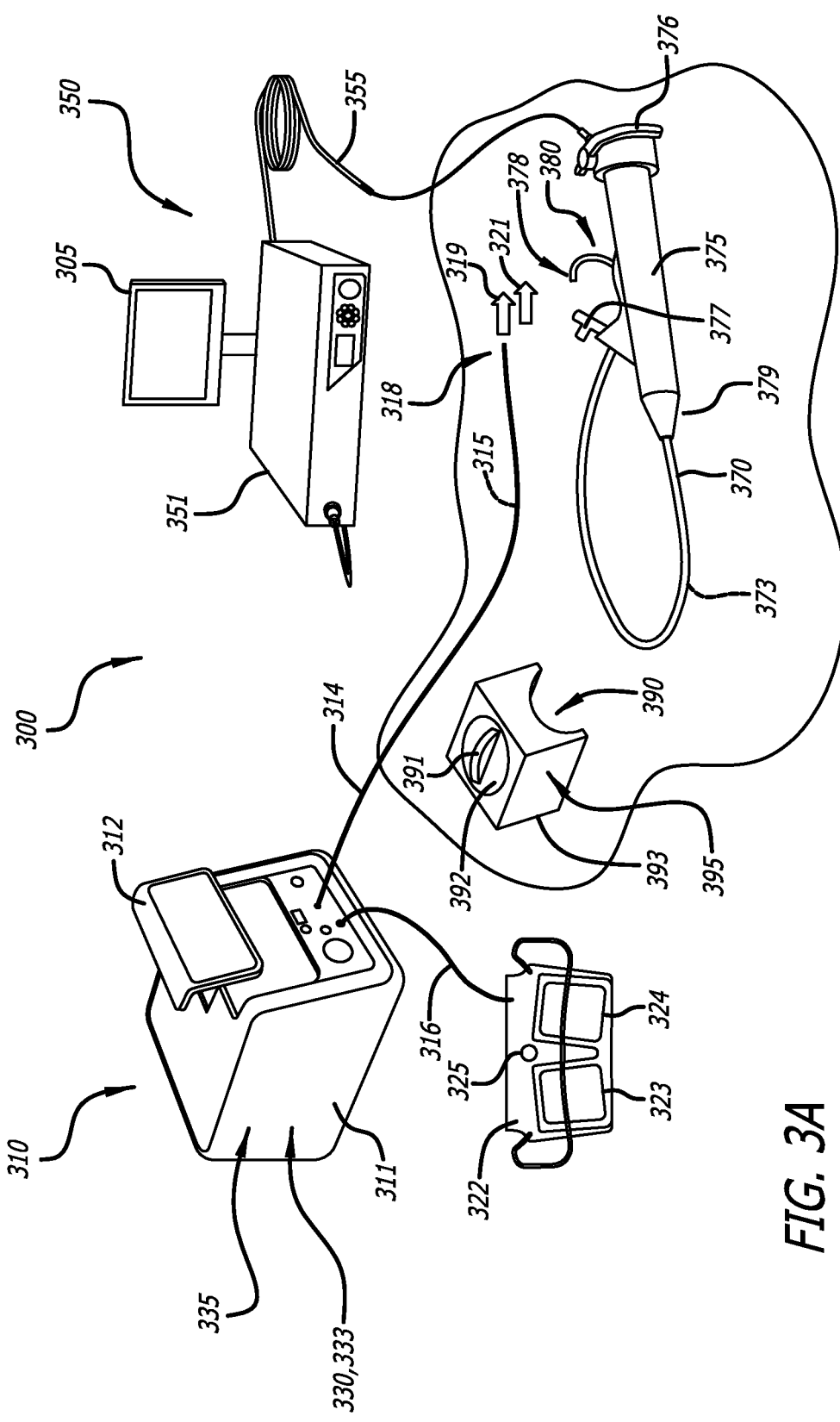
FIG. 3A illustrates a second embodiment of a medical system, in accordance with some embodiments.

FIG. 3A illustrates a second embodiment of a medical system, in accordance with some embodiments. The system 300 can, in certain respects, resemble components of the system 200 described in connection with FIGS. 2A-2B. It will be appreciated that all the illustrated embodiments may have analogous features. Accordingly, like features are designated with like reference numerals, with the leading digits incremented to "3." For instance, the handle is designated as "275" in FIGS. 2A-2B, and an analogous handle is designated as "375" in FIGS. 3A-3B. Relevant disclosure set forth above regarding similarly identified features thus may not be repeated hereafter. Moreover, specific features of system 200 and related components shown in FIGS. 2A-2B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the system 300. Any suitable combination of the features, and variations of the same, described with respect to the system 200 and components illustrated in FIGS. 2A-2B can be employed with the system 300 and components of FIGS. 3A-3B, and vice versa.

The system 300 includes two medical instruments, i.e., a first medical instrument 310 and the second medical instrument 350. By way of example in the illustrated embodiment, the first medical instrument 310 may be urological surgery laser instrument (hereinafter referred to as the laser instrument 310) and the second medical instrument 350 may a ureteroscope (hereinafter referred to as the ureteroscope 350). However, the first medical instrument 310 and a second medical instrument 350 may be any two medical instruments used in combination with each other to perform a medical procedure.

The laser instrument 310 includes a laser control module 311 operatively coupled with a flexible laser shaft 314. The laser shaft 314 includes a fiber optic laser 315 configured to define a laser beam 319 at the distal end 318 of the laser shaft 314. During operation the laser 315 is fired (i.e., activated) to turn "on" the laser beam 319. The laser beam 319 may be directed distally away from a distal end 318 as shown. The laser instrument 310 may also include an aiming light beam 321 directed distally away from the distal end 318 as shown. The aiming beam 321 may provide a visual indication of the aiming point of the laser beam 319. In other words, the aiming beam 321 may generate a visible indication (e.g., a dot on the tissue or foreign substance) of an impact location of the laser beam 319. In use, the operator may observe the dot via images provided by the ureteroscope 350.

The laser instrument 310 may include a graphical user interface (GUI) 312 via which an operator, such as the operator 30 depicted in FIG. 1, or an assistant may define a plurality of operating parameters for the laser instrument 310. The laser instrument 310 may also include a foot pedal interface 322 including a left foot pedal 323, a right foot pedal 324 and a state button 325. The foot pedal interface 322 may be coupled with the laser control module 311 via a foot pedal connection wire 316. In some embodiments, the foot pedal interface 322 may be wirelessly coupled with the laser control module 311 via a wireless module 335. As illustrated in FIG. 3A, the laser control module 311 and the foot pedal interface 322 are configured for operation outside of the sterile field 60. The laser shaft 314 may be sterilized and as such is configured for placement and use within the sterile field 60. In use, the laser shaft 314 extends across the barrier of the sterile field 60. The laser control module 311 control module 311 also includes remote communication logic 333 stored in memory 330 that may include a non-transitory computer-readable medium.

Figure 3B:
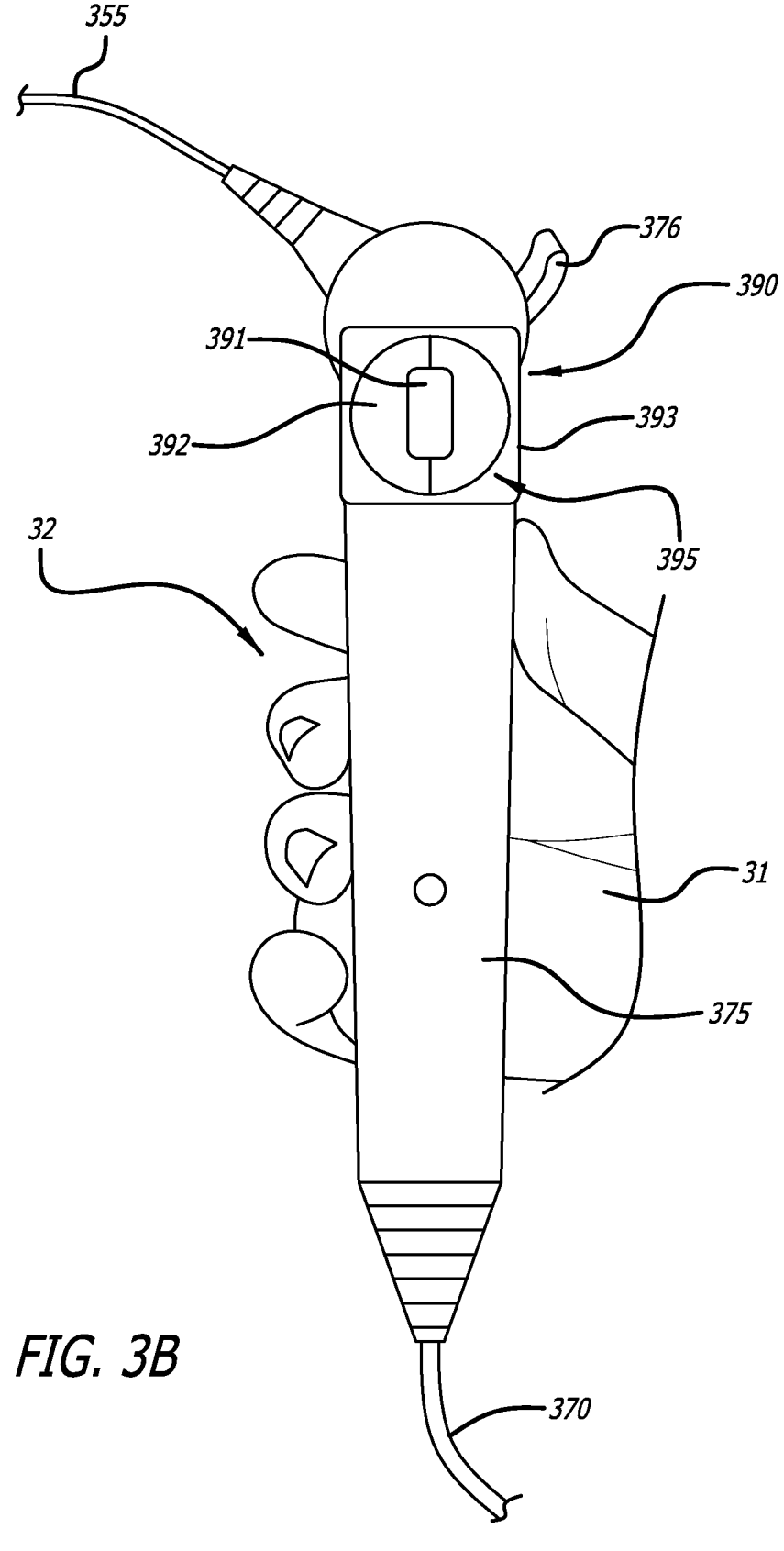
FIG. 3B is a detailed illustration of a remote interface of the first medical instrument of FIG. 3A attached to a handle of the second medical instrument, in accordance with some embodiments.

The laser instrument 310 includes a remote interface 390 wirelessly coupled with the laser control module 311. The remote interface 390 includes a housing 393 and a console 395 disposed therein. The housing 393 is configured for attachment to a handle of the ureteroscope 350 as described below. The remote interface 390 also includes a scrolling device 391 and a selecting device 392. The scrolling device 391 and a selecting device 392 are configured for manipulation by one or more extremities 32 of the operator's hand 31 (FIG. 3B). The remote interface 390 may be sterilized and therefore configured for placement and use within the sterile field 60.

With further reference to the FIG. 3A, the ureteroscope 350 includes a ureteroscope control module 351 operatively coupled with an elongate flexible shaft 370 configured for insertion within a urinary tract of the patient 50 (FIG. 1). The shaft 370 includes a camera (not shown) at a distal end 378 of the shaft 370. During operation, images acquired by the camera are rendered on a display 305 coupled with the ureteroscope control module 351. A working channel 373 extends along the shaft 370, and an access port 377 provides access to the working channel 373 at a proximal end 379 of the shaft 370.

A handle 375 is coupled to the shaft 370 at the proximal end 379 of the shaft 370. The handle 375 is configured for manipulation of the shaft 370 during use. The handle 375 includes a steering actuator 376 operatively coupled with an articulating distal portion (not shown) of the shaft 370, so that manipulation of the actuator 376 articulates the distal portion 380 of the shaft 370. A connection wire 355 couples the handle 375 with the ureteroscope control module 351. The ureteroscope control module 351 and the display 305 are configured for placement and use outside of the sterile field 60. The handle 375 and the shaft 370 are sterilized and are thus configured for placement and use within the sterile field 60. In use, the wire 355 extends across the barrier of the sterile field 60.

FIG. 3B is a detailed illustration of the handle 375 with the remote interface 390 attached thereto, in accordance with some embodiments. The handle 375 is configured to be grasped by the hand 31 of the operator. The steering actuator 376 is configured for manipulation by one or more extremities 32 of the hand 31, such as the thumb, for example.

The handle 375 is configured for attachment to the remote interface 390 as shown. The remote interface 390 may be attached to the handle 375 so that the operator 30 may access and manipulate the scrolling device 391 and a selecting device 392 with one or more extremities 32 of the hand 31. The remote interface 390 maybe attached to the handle via any suitable attachment mechanism such as an adhesive, a stretchable band extending around the handle 375, or corresponding snap fit features, for example.

Figure 4:
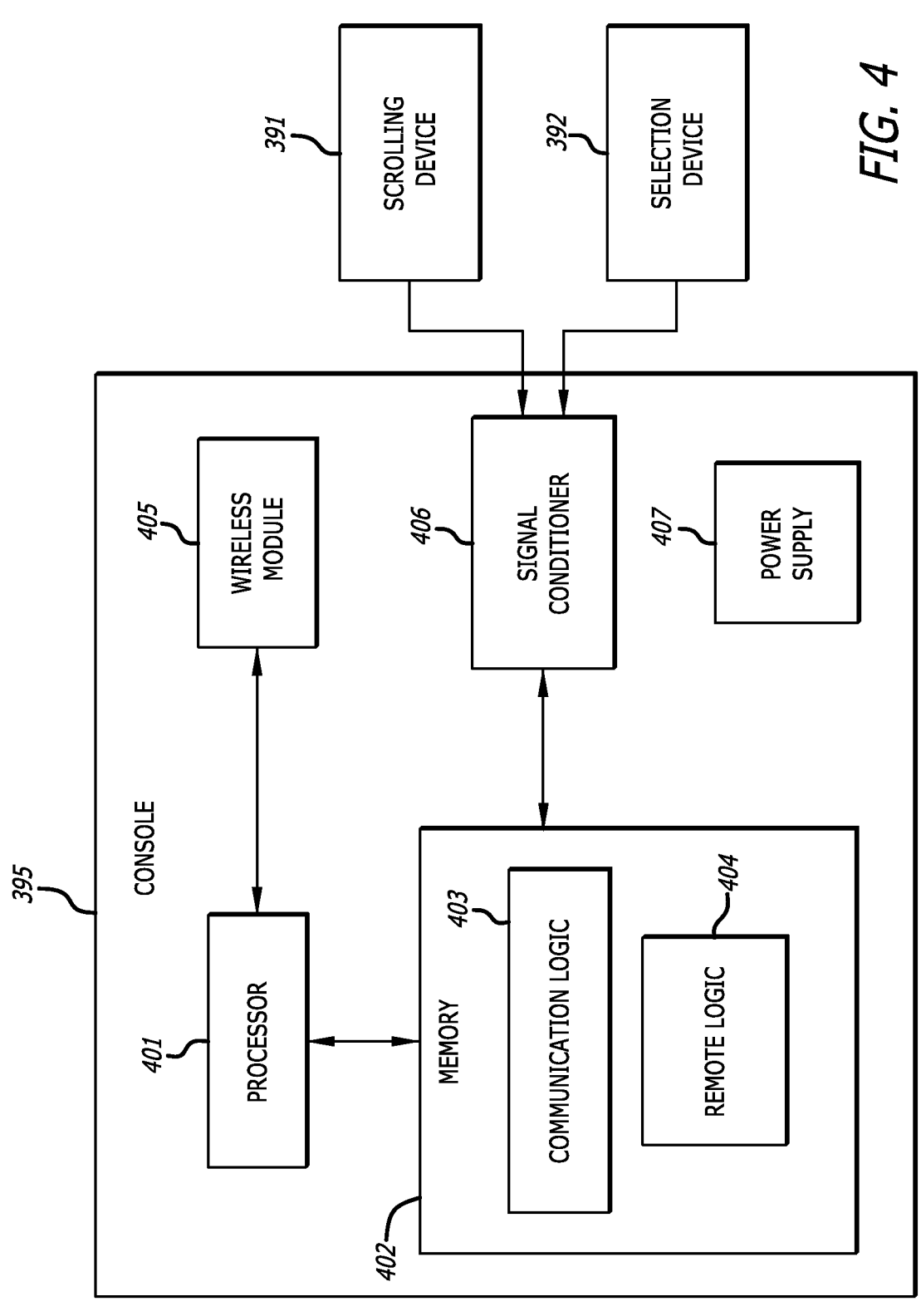
FIG. 4 is a block diagram of a console of the remote interface of FIGS. 3A-3B, in accordance with some embodiments.

FIG. 4 is a block diagram of the console 395 of the remote interface 390. The console 395 includes components to facilitate signal communication between the remote interface 390 and the laser control module 311. Communication logic 403 and remote logic 404 stored in memory 402 including a non-transitory computer-readable medium, cause operations of the processor 401 in accordance with operation of the remote interface 390. A signal conditioner 406 converts electrical signals from the scrolling device 391 and the selecting device 392 for operation by the processor 401. A wireless module 405 communicates with a corresponding wireless module 335 (FIG. 3A) of the laser control module 311 according to protocols defined by the communication logic 403 and the corresponding remote communication logic 333 stored in memory 330 of the laser control module 311. An internal power supply 407 (e.g., a battery) provides conditioned electrical power to the other components of the console 395. In an alternative embodiment, the remote interface 390 may be coupled with the laser control module 311 via a wired connection. In such an embodiment, the console 395 may include fewer components or may be omitted all together.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A system for providing a medical treatment, comprising:
   a first medical instrument, comprising:
      a first control module;
      a first patient interface member coupled with the first control module, the first patient interface member comprising a first distal end configured to engage a patient body; and
      a first operator interface operatively coupled with the first control module, the first operator interface configured to:
         set a plurality of operating parameters of the first medical instrument, and
         selectively activate and deactivate the first medical instrument in accordance with providing the medical treatment; and
   a second medical instrument, comprising:
      a second control module;
      a second patient interface member coupled with the second control module, the second patient interface member comprising a second distal end configured to engage the patient body; and
      a handle attached to the second patient interface member at a proximal end of the second patient interface member, wherein:
         the handle is configured to be grasped by a hand of an operator,
         the handle is configured to cause operations of the second distal end, and
         the handle comprises a second operator interface configured to set a subset of the plurality of operating parameters of the first medical instrument.

2. The system of claim 1, wherein the first patient interface member is coupled with the second patient interface member.

3. The system of claim 2, wherein the first distal end is disposed adjacent the second distal end.

4. The system of claim 1, wherein the second medical instrument is an endoscope.

5. The system of claim 1, wherein the second medical instrument is a ureteroscope.

6. The system of claim 1, wherein the first medical instrument comprises a laser.

7. The system of claim 6, wherein the laser includes a laser optical fiber extending along a length of the first patient interface member.

8. The system of claim 6, wherein the plurality of operating parameters comprises one or more of:

changing a state of the first medical instrument between a standby state and an active state;

selectively enabling and disabling the second operator interface;

changing a state of a laser aiming beam of the first patient interface member between on, off, and blinking states; or adjusting:

a laser pulse energy, a laser pulse frequency, a laser pulse width, an average power of the laser, or an intensity of the laser aiming beam.

9. The system of claim 8, wherein the subset of the plurality of operating parameters comprises one or more of:

changing the state of the first medical instrument between the standby state and the active state;

changing the state of the laser aiming beam between the on, off, and blinking states;

selectively enabling and disabling the second operator interface; or adjusting:

the laser pulse energy, the laser pulse frequency, the laser pulse width, the average laser power, or the intensity of the laser aiming beam.

10. The system of claim 1, wherein the first operator interface includes a graphical user interface.

11. The system of claim 1, wherein the first operator interface includes a foot pedal interface.

12. The system of claim 1, wherein in use:

the first operator interface is disposed outside of a sterile field, and the second operator interface is disposed within the sterile field.

13. The system of claim 1, wherein:

operations of the second distal end comprise steering the second distal end, and an actuator attached to the handle is configured to steer the second distal end.

14. The system of claim 13, wherein:

movement of the actuator is performed with one or more extremities of an operator's hand, and setting the subset of the plurality of operating parameters of the first medical instrument via the second operator interface is performed with the one or more extremities of the operator's hand.

15. The system of claim 1, wherein the second operator interface is wirelessly coupled with the first control module.

16. The system of claim 1, wherein the second operator interface comprises:

a scrolling device; and a selecting device.

17. The system of claim 1, wherein the second operator interface is selectively attachable to the handle.

* * * * *